United States Patent [19]

Sahota

[11] Patent Number: 5,044,369

[45] Date of Patent: Sep. 3, 1991

[54] BENT TOPLESS CATHETERS

[76] Inventor: Harvinder Sahota, 3861 Wisteria, Seal Beach, Calif. 90740

[21] Appl. No.: 510,472

[22] Filed: Apr. 18, 1990

Related U.S. Application Data

[63] Continuation of Ser. No. 301,179, Jan. 23, 1989, Pat. No. 4,976,691.

[51] Int. Cl.$^5$ .............................................. A61M 25/00
[52] U.S. Cl. ...................................... 128/658; 604/96; 604/280; 606/194
[58] Field of Search ................................ 128/656–658; 604/96–103, 280; 606/194

[56] References Cited

U.S. PATENT DOCUMENTS

| 2,862,498 | 12/1958 | Weekes | 604/280 X |
| 4,323,071 | 4/1982 | Simpson et al. | 604/53 X |
| 4,737,153 | 4/1988 | Shimamura et al. | 604/282 |
| 4,808,155 | 2/1989 | Mahurkar | 604/43 |
| 4,842,589 | 6/1989 | Facht et al. | 604/280 |

FOREIGN PATENT DOCUMENTS 8803817  6/1988  World Int. Prop. O. ............ 606/91

Primary Examiner—John D. Yasko
Assistant Examiner—Adam J. Cermak
Attorney, Agent, or Firm—Knobbe, Martens, Olson & Bear

[57] ABSTRACT

A topless catheter, which can be used as either a guiding catheter for guiding balloon dilatation catheters into a body lumen, or as a diagnostic catheter for conducting radio opaque dyes into a predetermined body lumen or both is disclosed. The topless catheter comprises a cylindrical catheter shaft, integrally connected to an arcuate topless guilding finger. The guiding finger is adapted for placement proximate to, or partially within a predetermined blood vessel for subselective placement of a dilatation balloon catheter. By virtue of the manner in which the guiding finger is configured, blood flow through the more distal arteries is substantially unimpeded without detracting from the support and guidance features, found in conventional guiding catheters.

5 Claims, 4 Drawing Sheets

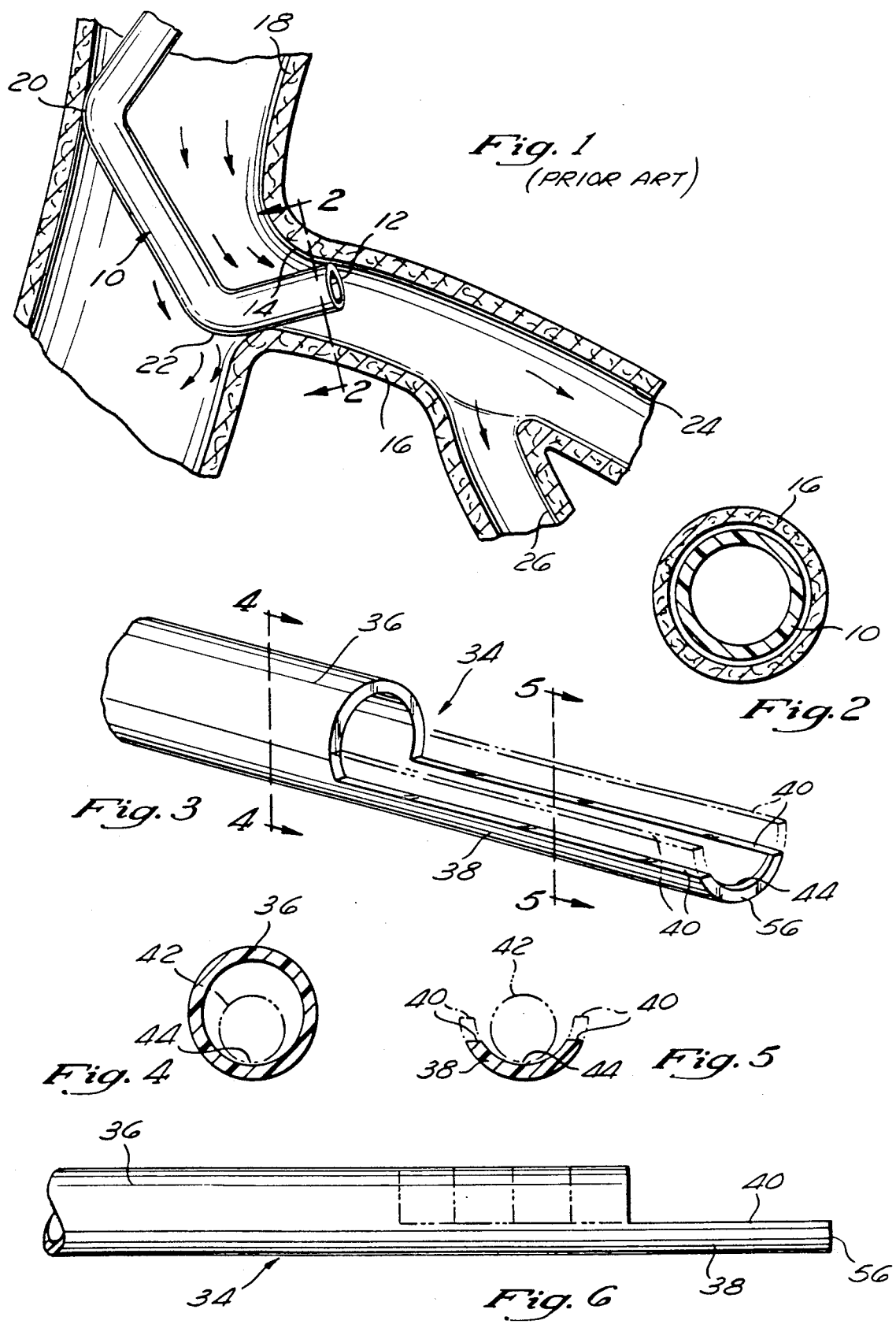

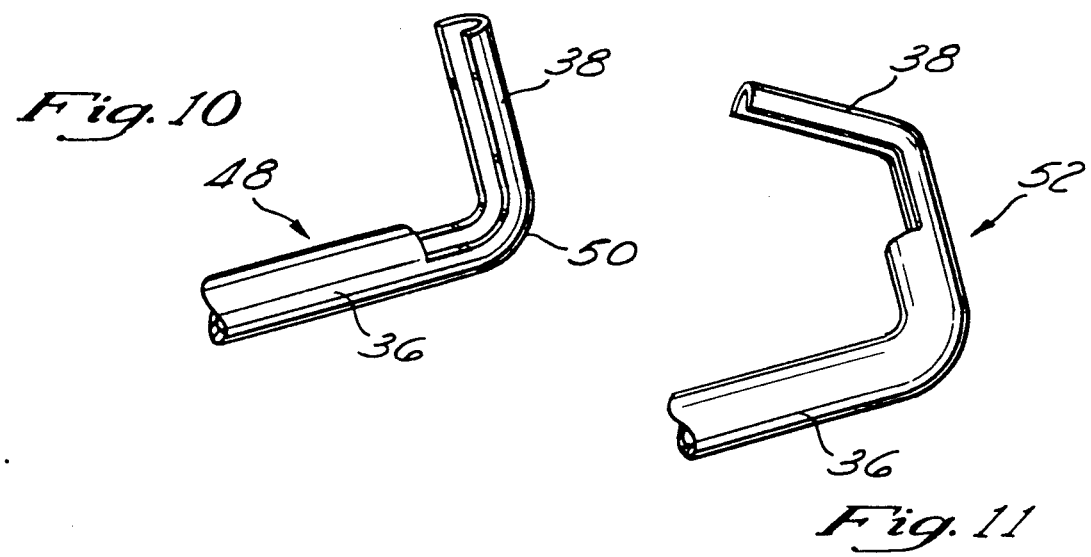
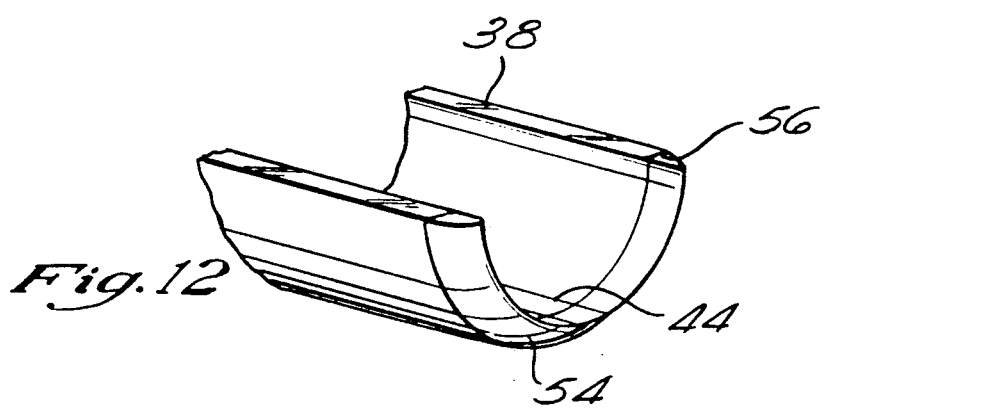
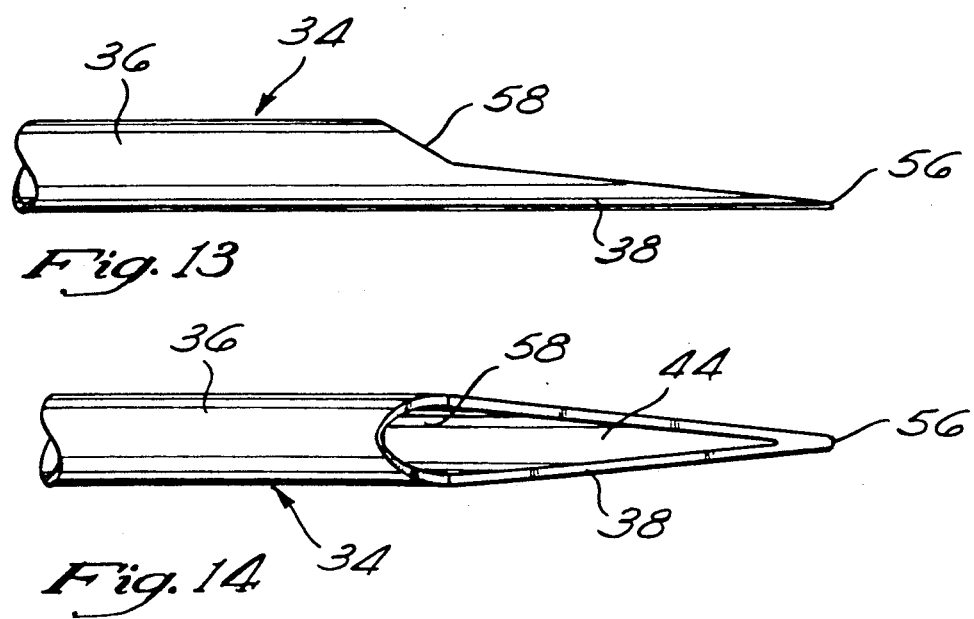

BENT TOPLESS CATHETERS

This application is a continuation of application Ser. No. 301,179, filed Jan. 23, 1989, now U.S. Pat. No. 4,976,691.

BACKGROUND OF THE INVENTION

The present invention relates generally to the field of catheters. More specifically, the present invention relates to a hollow catheter which may be used as a guiding sheath for balloon catheters, or for diagnostic purposes to conduct radio-opaque dyes to particular areas of the body, as for example, in angiography.

Percutaneous transluminal coronary angioplasty (PTCA) is a procedure for treating patients having stenotic, or constricted blood flow regions in the coronary arteries and has become a widely accepted therapeutic alternative to coronary bypass surgery. Performing a coronary angioplasty involves the difficulty of inserting a dilatation balloon catheter into the obstructed coronary artery. Because most balloon dilatation catheters are too flexible for direct insertion into a patient's blood vessel, the standard angioplasty process begins with the insertion of a guiding catheter, or sleeve into the obstructed vessel, under a local anesthesia. The guiding catheter is designed to provide a conduit through which a balloon dilatation catheter may be passed. In addition, the guiding catheter may be used as a diagnostic catheter to conduct radio-opaque dyes into the localized area to be dilated, so as to aid in determining when blood flow has been restored to an acceptable level.

The guiding catheter may be preformed into a bent configuration so as to better guide a dilatation catheter into the proper coronary orifice. The relatively stiff shaft of the guiding catheter is designed to provide the longitudinal support necessary to maintain tip stability as the balloon dilatation catheter is advanced into the appropriate coronary artery. Present guiding/diagnostic catheters for femoral PTCA can be thought of as being categorized into one of three general configurations: Judkins shapes, Amplatz shapes, and multipurpose shapes. The Judkins left catheter is commonly used for directing a balloon catheter into the left anterior descending artery, while the Judkins right catheter is adapted for use when treating the right coronary artery. The Amplatz catheter is most suited for use in the circumflex and right coronary arteries, and the multipurpose shapes are generally employed for vein grafts and some right coronary lesions. The purpose of the guiding catheter is not only to direct the balloon catheter into the diseased coronary artery, but also to provide a launching pad for exerting some pressure on the balloon catheter to force it through some very tight stenoses.

Once a guiding catheter is inserted into the femoral artery and positioned in the aorta proximate to the proper coronary orifice, a balloon dilatation catheter may be inserted and advanced into the diseased artery. However, sometimes the tip of the guiding catheter is advanced too far into the artery, impairing the blood supply distal to the guiding catheter. In addition, because the size and shapes of the various arteries vary substantially from patient to patient, it is often times impossible for the surgeon to place even the smallest guiding catheter proximate to the diseased artery without severely impeding blood flow.

FIG. 1 is illustrative of a presently available guiding catheter 10, having a left Judkins shape, in which the end 12 is positioned proximate the orifice 14 to the left main artery 16. Usually, the guiding catheter 10 is either pre-formed in one of the aforementioned configurations, as illustrated here, or is bent by the surgeon prior to introduction into the patients blood vessel. By altering the orientation of the tip 12 of the guiding catheter 10 with respect to the desired coronary orifice 14, the guiding catheter 10 can significantly aid in the subselective placement of a balloon dilatation catheter (not shown). As illustrated in FIG. 1, as the guiding catheter 10 is advanced through the aorta 18 the tip 12 is forced into the left main artery 16. One bend 20 will stabilize the catheter 10 with respect to the aorta 18 while the more distal bend 22 rests at the arterial orifice 14. As more clearly illustrated in FIG. 2, the guiding catheter 10 can block a substantial portion of the coronary orifice 14, thereby decreasing the amount of blood flow to the more distal vessels 24, 26. Depending on the diameter of the blood vessel 16, such blockage can severely impair blood flow therethrough. This creates a further dilemma for the surgeon, as the angioplasty procedure must be hastened or the guiding catheter 10 be partially withdrawn so as to increase the amount of blood flow.

Another common occurrence, especially in the right coronary artery, is the presence of stenotic lesions proximate the arterial orifice. As schematically illustrated in FIG. 15, the right coronary artery 28 is often times of the same diameter as even the smallest presently available guiding catheter 10. Thus, when the guiding catheter 10 is inserted through the aorta 18 and into the right coronary artery 28, it is blocked from further entry by the stenosis 30. Stenoses, in general are of varying degrees, shapes and sizes. When a stenosis 30 is present proximate to the arterial orifice 32, and the guiding catheter 10 is of the same size as that of the artery 28, then blood flow through that artery 28, as well as the more distal arteries (not shown), will be totally occluded. This is most undesirable in that the patient will then begin to experience chest pains, a drop in blood pressure, and may necessitate the emergency bypass surgery.

After performing a coronary angioplasty, it is often times desireable to ascertain the amount and rate of blood flow through the once-restricted vessel. Blood is not normally visible on an X-ray image because it has about the same radio density as that of the surrounding tissue. In angiographic procedures, the outlines of blood vessels are made visible on an X-ray image by injecting a bolus of contrast medium directly into the bloodstream in the region to be investigated. The injection of such a contrast medium into a blood vessel enables the circulation pattern to be made locally visible. Because the contrast medium is rapidly diluted in the blood circulation, an X-ray photo or a series of such photos must be taken immediately after the injection. On a sequential record of the X-ray image, the progress of the contrast medium can be followed so as to enable one to detect obstructions as well as to estimate blood flow in certain blood vessels. Preferably, the radio-opaque dye may be injected through the same guiding catheter used to guide the dilatation catheter. However, use of thus catheter is accompanied by the same flow restrictions. This is significant in that the measurement of the injected dye may produce faulty data due to the decrease in normal blood flow caused by the guiding catheter.

SUMMARY OF THE INVENTION

Briefly, the present invention is for a topless catheter which overcomes many of the drawbacks associated with present guiding and diagnostic catheters. The topless catheter of the present invention may be configured in any number of shapes, including, but not limited to straight, Amplatz, Judkins or multipurpose shapes. Significantly, the topless catheter of the present invention may be manufactured as such, or may take the form of a presently available catheter, modified to suit the particular vasculature of the patient being treated.

Preferably, the topless catheter of the present invention, comprises a polyurethane outer jacket which provides excellent curve retention. This is significant in that it allows the surgeon to selectively bend the end of catheter to aid in locating the proper coronary orifice. In addition, the catheter may be coated with teflon or some other smooth material so as to give the catheter some lubricity and aid in the ease of insertion. When forming the topless portion of the guiding catheter, it is important that the integrity of the bottom, or guiding finger be maintained so as to give the guiding catheter some stability. The length of the topless portion, as well as the depth of the cut walls be of various proportions, depending upon the anatomy of the patient's blood vessels. Advantageously, the guiding finger of the catheter provides less of an obstruction at the coronary orifice so as to enable a steady flow of blood to continue flowing through the diseased blood vessel as well as adjacent blood vessels which may stem from the same main branch.

BRIEF DESCRIPTION OF THE DRAWINGS

These and other objects, features and advantages of the present invention should become apparent from the ensuing description, when considered with the accompanying drawings, in which:

FIG. 1 is a partial cross-sectional view, schematically illustrating the left main artery, having inserted therein a presently available prior art guiding/diagnostic catheter;

FIG. 2 is a cross-sectional view, taken along line 2—2 of FIG. 1, illustrating a reduced blood flow passage;

FIG. 3 is a perspective view of a straight topless catheter, consistent with one aspect of the present invention, showing in dotted lines, varying depths of the guiding finger;

FIG. 4 is a cross-sectional view, taken along line 4—4 of FIG. 3, showing in dotted lines, the positioning of a dilatation catheter within the guiding catheter;

FIG. 5 is a cross-sectional view, taken along line 5—5 of FIG. 3, illustrating the arcuate guiding finger of the topless guiding/diagnostic catheter of the present invention;

FIG. 6 is a side view of the topless catheter illustrated in FIGS. 3-5, showing, in dotted lines, varying lengths of the guiding finger;

FIG. 10 is a perspective view of an alternative pre-formed of the topless catheter consistent with the present invention;

FIG. 11 is a perspective view of another pre-formed topless catheter, consistent with the present invention;

FIG. 12 is a partial perspective view of a flexible tipped topless catheter;

FIG. 13 is a side view of an alternative guiding/diagnostic catheter, having a diamond-shaped guiding finger;

FIG. 14 is a top view of the topless catheter illustrated in FIG. 13;

DETAILED DESCRIPTION OF THE PREFERRED EMBODIMENT

Figure 7:
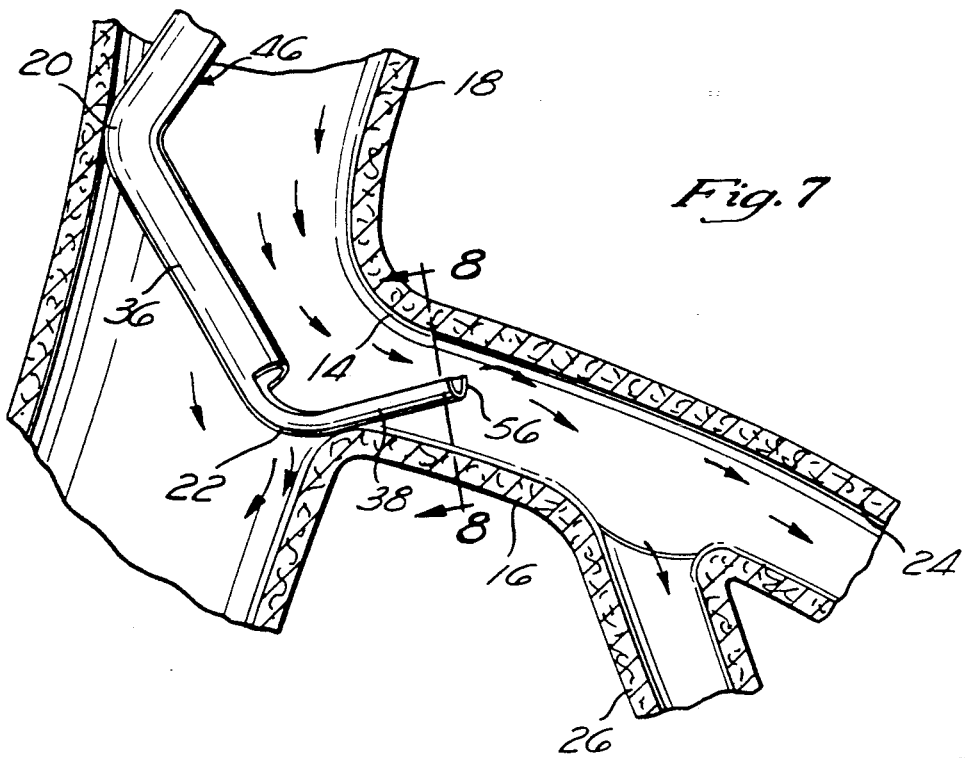
FIG. 7 is a partial cross-sectional view, schematically illustrating the left main artery, having inserted therein a topless catheter, consistent with one aspect of the present invention.

Referring now to the drawings in detail, wherein like reference numerals designate like elements throughout the several views thereof, there is shown generally at 34 in FIGS. 3-6, a topless catheter, which can be used as either a guiding catheter for guiding a balloon dilatation catheter into a body lumen or a diagnostic catheter for conducting radio opaque dyes into a predetermined body lumen, embodying the present invention in a preferred form. As illustrated in the drawing figures, the topless catheter 34 comprises an axially elongate cylindrical shaft 36 integrally connected to an arcuate topless portion 38, which forms a guiding finger. A significant advantage of this invention is that it does not interfere with the conventional procedure in which the guiding catheter 34 is used to support and guide a dilatation balloon catheter (not shown).

FIGS. 3 and 5 illustrate, in dashed lines, that the walls 40 of the guiding finger 38 may be of varying heights. Shown in cross-section, in FIGS. 4 and 5, a dilatation balloon catheter 42 is illustrated in phantom, disposed within the topless catheter shaft. Significantly, as the dilatation catheter 42 is advanced through the elongate catheter shaft 36, it frictionally engages the inner bottom surface 44. Thus, as the dilatation catheter 42 emerges from the cylindrical portion 36 of the topless catheter 34, it continues to be guided by the bottom surface 44 of the arcuate guiding finger 38 in the same manner as though the topless portion of the guiding catheter 34 was still in place. FIG. 6 illustrates that, in addition to varying the height of the walls 40 of the arcuate guiding finger 38, the length may also be varied.

Preferably, the topless catheter 34 of the present invention is manufactured with a polyurethane outer jacket, which provides excellent curve retention. Thus, the surgeon may place bends along the shaft of the catheter 34, as is commonly done with standard guiding catheters, so as to facilitate proper angulation for alignment with the desired coronary orifice. This feature aids the surgeon in better positioning the topless catheter 34 within the blood vessel, proximate the desired arterial orifice.

Figure 8:
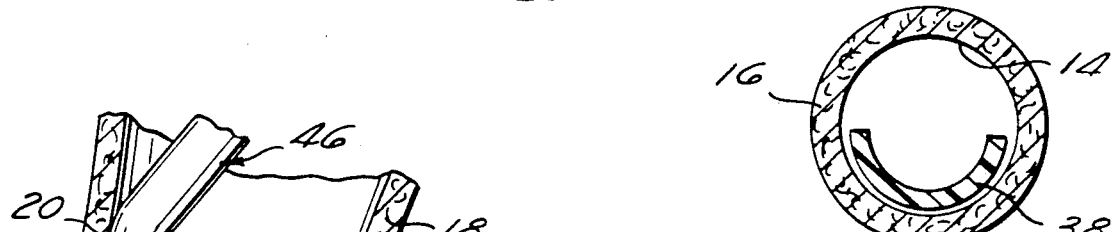
FIG. 8 is a cross-sectional view, taken along line 8—8 of FIG. 7, illustrating the unimpeded path through which blood may continue to flow.

Alternatively, the topless catheter 34 of the present invention may be preformed into predetermined different configurations, such as the representative embodiments of the catheter illustrated in FIGS. 7 ∝ 11. FIG. 7 illustrates a diagnostic catheter 46, having an arcuate guiding finger 38 in accordance with this invention which is bent at an angle with respect to the catheter body 36. This catheter is shown positioned within the aorta 18, proximate to the orifice 14 to the left main artery 16. As illustrated in cross section in FIG. 8, the topless diagnostic catheter 46 has a substantially decreased cross-section so that it does not significantly impede the normal circulation pattern of the blood flow through the artery 16. This is quite important in that often times, as illustrated, there exists more than one major arterial branch 24, 26 stemming from a single orifice 14. If the guiding/diagnostic catheter 46 were to occlude the left main artery 16, the more distal branches 24, 26 would also be occluded. Such occlusion can induce symptoms of myocardial infarction or, worse yet, an actual heart attack. Further, when a radio-opaque dye is conducted through the diagnostic catheter 46, the normal flow of blood will carry the dye into the area to be observed. If the blood flow were impeded, less of the dye would be present in the desired area, and would take a longer time to reach the intended destination.

Figure 9:
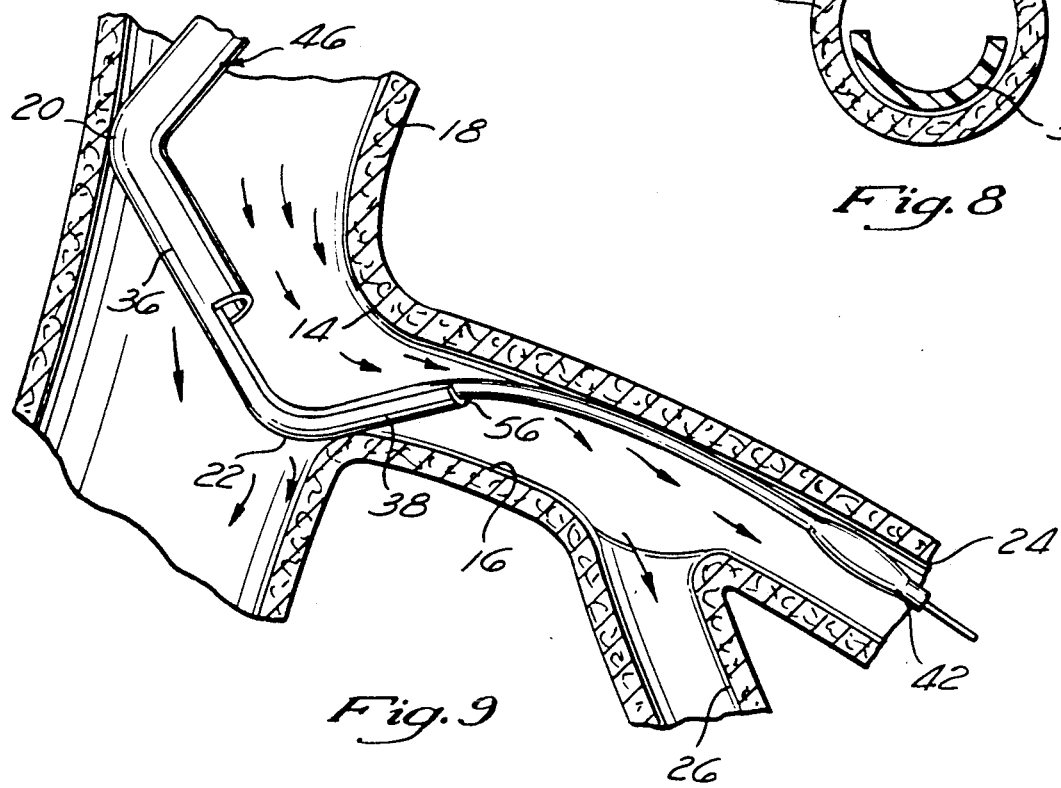
FIG. 9 is a partial cross-sectional view, schematically illustrating the left main artery, having inserted therein a pre-formed topless guiding catheter through which a balloon dilatation catheter has been advanced.
Figure 15:
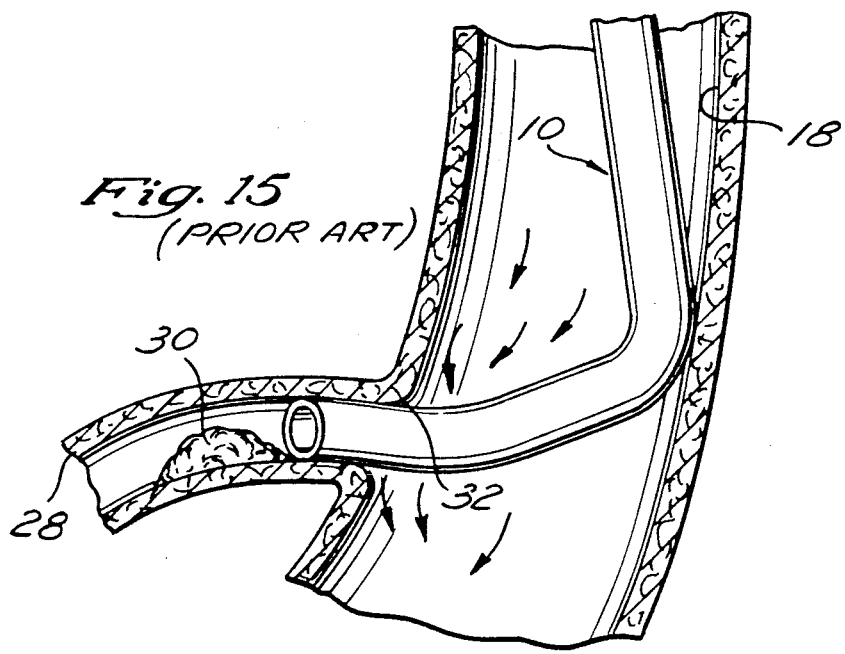
FIG. 15 is a partial cross-sectional view, schematically illustrating the right coronary artery with a stenotic region proximate the orifice, having inserted therein a presently available prior art guiding/diagnostic catheter.

FIG. 9 illustrates the manner in which the balloon dilatation catheter 42 is guided around a corner from the aorta 18 through the coronary orifice 14 and into the artery 16 by use of the guiding catheter 46. As the guiding catheter 46 is advanced through the aorta 18, the surgeon may take advantage of the bends 20, 22 placed along the shaft 36 to stabilize the guiding catheter 46 with respect to the orifice 14. Advantageously, the same catheter 46 may be used to both conduct dyes into the desired artery 16 as well as to guide a balloon dilatation catheter 42 into a more distal artery 20, toward a stenotic lesion (not shown). By virtue of the topless configuration, the blood flow through the more distal arteries 24, 26 is substantially unimpeded.

Figure 16:
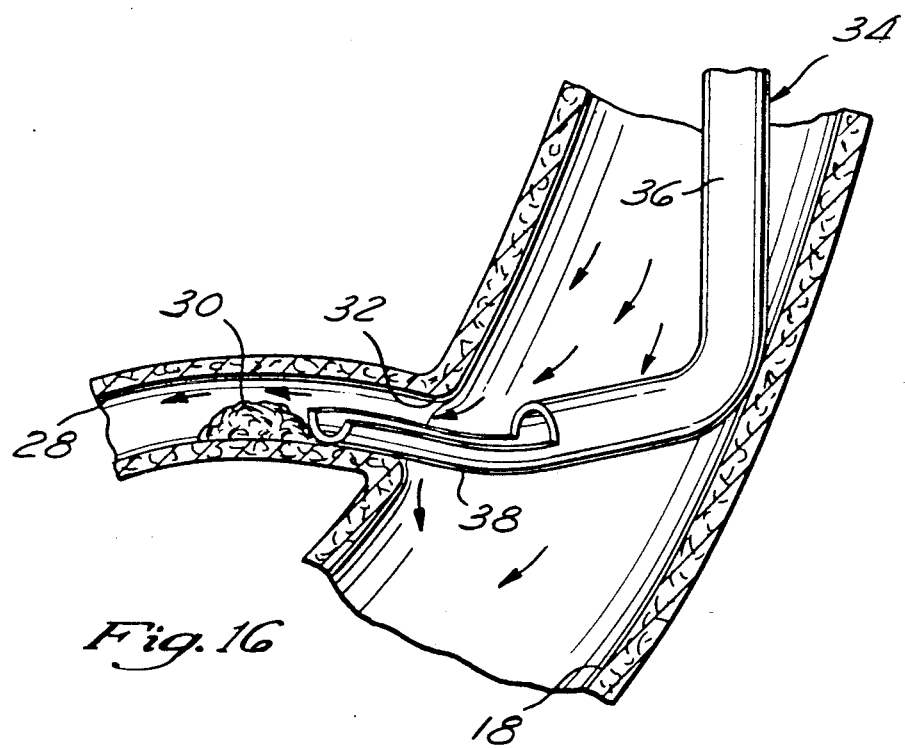
FIG. 16 is a partial cross-sectional view, schematically illustrating the right coronary artery, with a stenotic region proximate the orifice, having inserted therein a guiding/diagnostic catheter consistent with the present invention.

FIG. 16 illustrates the topless guiding catheter 34 of the present invention as positioned proximate to the right coronary artery 28. As illustrated in the drawing figure, the right coronary artery 28 is shown having a stenosis 30, proximate to the coronary orifice 32. The presence of this stenosis 30 has already impeded the blood flow through this artery 28, making it most desirable to maintain what little flow already exists. Advantageously, the topless catheter 34 of the present invention may be positioned in the artery 28 such that the arcuate guiding finger 38 is in alignment with the stenosis 30, so as not to diminish the presently limited flow.

The particular shape into which the guiding/diagnostic catheter 34 is bent will depend upon the particular requirement of the medical procedure. FIG. 10 illustrates a topless catheter 48 in which the end portion is preformed into a single, substantially right-angle bend 50, and FIG. 11 illustrates a topless catheter preformed into a substantially J-shaped configuration 52. In all cases, however, it will be apparent that the topless configuration will present a diminished cross-sectional blocking area within the body lumen without sacrificing the utility of the catheter.

All blood vessels have a lining of very flattened cells, known as endothelial cells, the integrity of which is essential to normal blood flow. Damage or injury to the endothelial layer promotes the adherence of blood cells passing through the vessel at the point of injury, which may result in serious clotting, or the formation of additional stenotic lesions. Thus, in an effort to reduce to a minimum the amount of trauma induced by the insertion of a guiding or diagnostic catheter 34 into a patient's blood vessel, it may be desirable to incorporate a soft tip 54 which may be secured to the distal end 56 of the arcuate guiding finger 38, as illustrated in FIG. 12. The tip 54 may, for example, be formed from a substantially malleable Poly Vinyl Chloride (PVC) compound, which may be RF welded to the distal end 56 of any of the above-referenced topless catheters.

FIGS. 13 and 14 illustrate an additional embodiment of the topless catheter 34 of the present invention. In this embodiment, the topless portion 58 of the catheter tapers toward the distal end 56 of the catheter 34. This configuration may prove less obstructive to normal blood flow, by virtue of the tapered end. The positioning of the guiding catheter 34 is accomplished in much the same way as the above-referenced catheters, the successful placement of which rests in the skilled hands of the person performing the procedure.

It will be appreciated that certain structural variations may suggest themselves to those skilled in the art. The foregoing detailed description is to be clearly understood as given by way of illustration, the spirit and scope of this invention being solely limited by the appended claims.

What is claimed is:

1. A guiding catheter for use in the diagnosis and treatment of arterial stenosis, constructed and arranged to i) conduct ratio opaque dyes into a predetermined blood vessel and ii) guide a balloon dilatation catheter into the blood vessel to relieve the stenosis, said guiding catheter comprising:

an axially elongate cylindrical shaft, having a proximal end and a distal end; and an arcuate topless section, integrally connected to said distal end of said shaft, said distal topless section being preformed into a single, substantially right-angle bend.

2. A guiding catheter for use in the diagnosis and treatment of arterial stenosis, constructed and arranged to i) conduct ration opaque dyes into a predetermined blood vessel and ii) guide a balloon dilatation catheter into the blood vessel to relieve the stenosis, said guiding catheter comprising:

an axially elongate cylindrical shaft, having a proximal end and a distal end; and an arcuate topless section, integrally connected to said distal end of said shaft, said distal topless section being preformed into a substantially J-shaped configuration.

3. A guiding catheter for use in the diagnosis and treatment of arterial stenosis, constructed and arranged to i) conduct ratio opaque dyes into a predetermined blood vessel and ii) guide a balloon dilatation catheter into the blood vessel to relieve the stenosis, said guiding catheter comprising:

an axially elongate cylindrical shaft, having a proximal end and a distal end, said shaft being hallow and comprising a polyurethane outer jacket for providing strength, rigidity and curve retention properties to said shaft; and an arcuate topless section, integrally connected to said distal end of said shaft.

4. A catheter system, comprising:

an axially elongate, hallow cylindrical shaft, having a proximal end and a distal end, said shaft adapted for insertion into a predetermined blood vessel;

an arcuate topless section, integrally connected to said distal end of said shaft and forming an angle therewith, said topless section constructed and arranged to sit at a predetermined vascular orifice a balloon dilatation catheter, adapted for insertion into said hallow shaft, so as to be guided through said vascular orifice and into said blood vessel without substantially impeding the normal flow of blood therethrough.

5. A catheter sheath, comprising:

an axially elongate hollow cylindrical shaft, adapted for insertion into a body lumen, said catheter shaft comprising a polyurethane outer jacket, adapted to retain predetermined bends so as to aid in placing said sheath proximate to a predetermined coronary orifice; and a semi-cylindrical guiding finger, integrally connected to one end of said shaft, said guiding finger retaining the width of said shaft, but exhibiting a smaller cross-sectional area than that of said shaft, so as to be less obstructive to bodily fluids flowing through said lumen.

* * * * *